(12) United States Patent
Han (10) Patent No.: US 10,399,912 B2
(45) Date of Patent: Sep. 3, 2019

(54) SELECTIVE OLIGOMERIZATION REACTION PROCESS OF ETHYLENE (71) Applicant: Taek Kyu Han, Daejeon (KR)

(72) Inventor: Taek Kyu Han, Daejeon (KR)

( * ) Notice: Subject to any disclaimer, the term of this patent is extended or adjusted under 35 U.S.C. 154(b) by 12 days.

(21) Appl. No.: 15/754,538

(22) PCT Filed: Sep. 16, 2015

(86) PCT No.: PCT/KR2015/009716
§ 371 (c)(1),
(2) Date: Feb. 22, 2018

(87) PCT Pub. No.: WO2017/039048
PCT Pub. Date: Mar. 9, 2017

(65) Prior Publication Data
US 2018/0237360 A1 Aug. 23, 2018

(30) Foreign Application Priority Data
Sep. 3, 2015 (KR) .................. 10-2015-0125153

(51) Int. Cl.
B01D 3/06 (2006.01)
B01D 3/14 (2006.01)
(Continued)

(52) U.S. Cl.
CPC .............. C07C 2/08 (2013.01); C07C 7/177 (2013.01); C07C 9/14 (2013.01); C07C 11/02 (2013.01);
(Continued)

(58) Field of Classification Search
None
See application file for complete search history.

(56) References Cited

U.S. PATENT DOCUMENTS 5,541,270 A 7/1996 Chinh et al.
2007/0185358 A1 8/2007 Buchanan et al.
(Continued)

FOREIGN PATENT DOCUMENTS

JP 2014177423 A 9/2014
KR 1020060002741 A 1/2006
(Continued)

OTHER PUBLICATIONS

Bollmann, A. et al., "Ethylene Tetramerization: A New Route to Produce 1-Octene in Exceptionally High Selectivities," Journal of the American Chemical Society, vol. 126, No. 45, Nov. 1, 2004, Published Online Oct. 20, 2004, 2 pages.
(Continued)

*Primary Examiner* — In Suk C Bullock
*Assistant Examiner* — Ali Z Fadhel
(74) *Attorney, Agent, or Firm* — McCoy Russell LLP (57) ABSTRACT The present invention relates to a commercial reaction process for the selective oligomerization reaction of ethylene, and a method for efficiently removing reaction heat to be generated in a reaction and regulating the temperature of the reactor and, more specifically, to an oligomerization reaction process of ethylene by circulating a liquid mixture in the reactor, separating unreacted ethylene from this circulation flow by an apparatus for separating unreacted ethylene from the circulation flow, and then cooling the remaining mixture and reintroducing it to the reactor, thereby removing the reaction heat in the reactor and allowing temperature control.

10 Claims, 4 Drawing Sheets (51) Int. Cl.
  *C07C 2/08* (2006.01)
  *C07C 9/14* (2006.01)
  *C08F 6/10* (2006.01)
  *C08F 6/14* (2006.01)
  *C07C 11/02* (2006.01)
  *C07C 7/177* (2006.01)
  *C08F 10/02* (2006.01)

(52) U.S. Cl.
  CPC .................. *C08F 6/10* (2013.01); *C08F 6/14* (2013.01); *C08F 10/02* (2013.01); *B01D 3/06* (2013.01); *B01D 3/14* (2013.01); *C08F 2500/02* (2013.01); *C08F 2500/03* (2013.01); *Y02P 20/52* (2015.11)

(56) References Cited

U.S. PATENT DOCUMENTS

| | | | |
|---|---|---|---|
| 2012/0142089 A1 | 6/2012 | Park | |
| 2012/0330078 A1* | 12/2012 | Hofmann | C07C 2/08 585/520 |
| 2015/0126790 A1* | 5/2015 | Venter | C07C 2/36 585/511 |

FOREIGN PATENT DOCUMENTS

| | | |
|---|---|---|
| KR | 1020090017929 A | 2/2009 |
| KR | 1020100087913 A | 8/2010 |
| KR | 1020130105126 A | 9/2013 |
| KR | 1020150088249 A | 7/2015 |
| WO | 2004056479 A1 | 7/2004 |

OTHER PUBLICATIONS

Kuhlmann, S. et al., "Chromium catalyzed tetrameritization of ethylene in a continuous tube reactor—Proof of concept and kinetic aspects," Journal of Catalysis, vol. 262, No. 1, Feb. 15, 2009, Published Online Jan. 8, 2009, 9 pages.

ISA Korean Intellectual Property Office, International Search Report Issued in Application No. PCT/KR2015/009716, dated Nov. 26, 2015, WIPO, 4 pages.

* cited by examiner

SELECTIVE OLIGOMERIZATION REACTION PROCESS OF ETHYLENE

CROSS-REFERENCE TO RELATED APPLICATIONS

The present application is a U.S. National Phase of International Patent Application Serial No. PCT/KR2015/009716 entitled "SELECTIVE OLIGOMERIZATION REACTION PROCESS OF ETHYLENE," filed on Sep. 16, 2015. International Patent Application Serial No. PCT/KR2015/009716 claims priority to Korean Patent Application No. 10-2015-0125153, filed on Sep. 3, 2015. The entire contents of each of the above-cited applications are hereby incorporated by reference in their entirety for all purposes.

TECHNICAL FIELD

The present invention relates to a commercialized reaction process for a selective ethylene oligomerization in which the exothermic heat by the reaction is efficiently removed, and the temperature of the reactor is controlled, and more particularly, to an oligomerization reaction process of ethylene by circulating a liquid mixture in the reactor, separating unreacted ethylene from this circulation flow by an apparatus for separating unreacted ethylene from the circulation flow, and then cooling the remaining mixture and reintroducing it to the reactor, thereby removing the reaction heat in the reactor and allowing temperature control.

BACKGROUND ART

A process technology for oligomerizing ethylene is commercially very useful. Among alpha-olefins prepared by an oligomerization process of ethylene, alpha-olefins currently expensive in the market are 1-hexene and 1-octene, which are important commercial raw materials, mainly used as a comonomer for preparing high value-added linear low-density polyethylene (LLDPE).

However, a conventional ethylene oligomerization process technology using an aluminum or nickel catalyst typically produces alpha-olefins having a large distribution of carbon atoms depending on a Schulz-Flory or Poisson product distribution. Therefore, the conventional technique for producing a large distribution of alpha-olefins has a limitation in producing alpha-olefins having a high value in the market with high selectivity.

Accordingly, since it was found out that ethylene may be selectively trimerized or tetramerized by transition metal catalysis to prepare 1-hexene and 1-octene in a high yield, research thereon has been actively conducted. In this regard, most of the known catalyst techniques use a chromium-based transition metal catalyst. Korean Patent Laid-Open Publication No. 10-2006-0002741 disclosed that excellent ethylene trimerization activity is possible using a PNP ligand containing a nonpolar substituent at an ortho position of a phenyl ring attached to phosphorus like (o-ethylphenyl)$_2$PN(methyl)P(o-ethylphenyl)$_2$. In addition, International Patent Publication No. WO2004-056479 disclosed that ethylene may be tetramerized by a chromium-based catalyst containing a PNP ligand having no substituent in a phenyl ring attached to phosphorus to improve production selectivity of 1-octene, and also discloses (phenyl)$_2$PN(isopropyl)P(phenyl)$_2$, etc. as an example of a heteroatom ligand used in a catalyst for such tetramerization. This patent document disclosed that though a ligand complexed chromium-based catalyst containing a heteroatom such as nitrogen and phosphorus has no polar substituent in a hydrocarbyl or heterohydrocarbyl group attached to a phosphorus atom, ethylene may be tetramerized by the catalyst to produce 1-octene with selectivity of more than 70% by mass. According to another known article, it is known in the art that when a catalyst complex was previously synthesized by a ligand having a —P—N—P— type backbone having a heteroatom between two P's and a chromium precursor and used to carry out an ethylene oligomerization reaction, the result was that there was no big change of activity and selectivity from the result of injecting the ligand and the chromium precursor separately to the oligomerization reactor. (*J. Am. Chem. Soc.*, 2004, 126, 14712)

Meanwhile, Korean Patent Laid-Open Publication No. 10-2009-0017929 (SK Holdings) disclosed that since in a P—X—P ligand, it is due to the electronic and geometric structure of a connection structure between two phosphorus (P) atoms coordinated to chromium that trimerization or tetramerization may be selectively increased in an ethylene oligomerization reaction using a chromium-based catalyst, the most appropriate geometric structure is a connection structure of S,S—(P—C(alkyl)-C(alkyl)-P—) or R,R—(P—C(alkyl)-C(alkyl)-P—). However, the ligand of P—C—C—P— structure has a limitation in activity and selectivity, when it is injected separately from a transition metal to an ethylene oligomerization reaction medium. The reason is that the backbone structure does not possess an unshared electron pair as a pure carbon atom, and a phosphine atom giving an electron to a transition metal has a limited coordination direction to the transition metal around it due to the chiral carbon in the backbone structure, and thus, there is difficulty in forming a coordination bond with the transition metal in a reaction medium. As a result, the geometric and electronic effect of the P—C—C—P backbone structure is as follows: when the transition metal precursor and the P—C—C—P backbone ligand structure are injected separately to the ethylene oligomerization reaction medium as a catalyst like the P—N—P ligand, the number of molecules of the transition metal precursor to be converted to a catalytic active site is substantially decreased unlike the P—N—P ligand, and this results in the decrease of the activity and selectivity in trimerization or tetramerization of ethylene.

Therefore, it is known from Korean Patent Laid-Open Publication No. 2010-0087913 (SK Holdings) that a chiral ligand having a —P—C—C—P— backbone structure is previously reacted with a transition metal precursor to synthesize a chiral ligand-transition metal complex in a substantially pure form, which is then injected to an ethylene oligomerization reactor, for overcoming the limitation in improving catalyst activity. As a result, it was surprisingly found that a reaction activity was increased by 10 times or more, and the produced amount of polyethylene polymer byproduct was decreased by $\frac{1}{10}$ times or less due to high selectivity. Consequently the polymer content after reaction may be decreased to 0.1% by mass or less, and due to the low production rate of the byproduct, the commercial process for production may be very simplified, for example, the purification process may be simplified.

According to the recent catalyst trend, as the technique for producing the expensive 1-hexene or 1-octene by selective ethylene oligomerization using a chromium-based transition metal as a catalyst has been desperately needed in the market, as compared to the conventional technique for producing various α-olefins in a large broad distribution using an alkyl aluminum or nickel-based catalyst, many attempts have been made to commercialize the technique in the related industry. As an example thereof, Sasol Technology published how the reaction conditions such as the temperature and ethylene concentration was effected on the selectivity and activity of 1-hexene and 1-octene using a continuous tubular reactor (plug flow tubular reactor, PFTR) in comparison with that using a semi-batch reactor (Journal of Catalysis, 262, 83, 2009). In the view of commercialization, the result was that since the ethylene concentration is rapidly decreased in the PFTR reactor, as the position of the tube is more distant from an ethylene inlet, it is difficult to efficiently adjust the conversion rate and the selectivity.

The crucial problem to be solved for commercializing ethylene oligomerization is to minimize a polyethylene polymer which is the byproduct produced in the oligomerization reaction and get it out of the reactor. In this regard, Korean Patent Laid-Open Publication No. 2010-0087913 disclosed that in the case of using an oligomerization catalyst having high selectivity, the production rate of the polyethylene polymer byproduct is very low, i.e., 0.1% by weight or less, and thus, the produced polymer byproduct are a precipitate in the form of small particles and present as a suspension solution in the reaction medium, thereby easily releasing the byproduct out of reactor without fouling or plugging. However, according to the published document, when the temperature is abruptly lowered in the reaction process, serious fouling may occur. U.S. Patent Application Publication No. 2012-0142089 disclosed that when removing the heat energy arising from the reaction by a cooling coil on the reactor surface in the reaction process, a heating coil is further attached so that there is no drastic temperature drop, thereby preventing from fouling. However, the cooling coil coexists with the direct heating coil on the reactor surface, so that the reaction mixture in the reactor is in direct contact with the surface of the cooling coil and heating coil, thereby having a limitation in overcoming the partly drastic temperature drop and rise of the reaction mixture.

DISCLOSURE

Technical Problem

There is a significant problem to overcome in order to commercialize the ethylene oligomerization process using a chromium-based transition metal catalyst system. This problem is that some polyethylene polymer which is a byproduct produced from an oligomerization reaction fouls the inner surface and an agitator in a reactor, or a high molecular weight polyethylene byproduct representing a solid phase at room temperature which should be released out of the reactor with an alpha-olefin (α-olefin) product and a reaction solvent plugs the outflow tract while being released. In order to avoid the problem, the produced polyethylene byproduct should be hardly present, or even in the case of being produced, it should be spread into the liquid phase as a suspended solid phase, so that it does not foul the surface and is released well together with the α-olefin product without plugging the outflow tract.

However, considering the cause of production of the polyethylene byproduct from the catalytic point of view, it is because the catalytic active site is abnormally changed depending on the reaction environment. That is, the chromium-based transition metal catalyst system for ethylene oligomerization reaction should be activated using partially oxidized alkyl aluminum such as alkyl aluminum or methylaluminoxane (MAO) or modified methylaluminoxane (MMAO). Since the activated catalyst in the reactor is present in a very unstable state, when the reactor is not maintained in a constant and uniform state, the activated catalyst may be transformed or deactivated. The transformed catalyst may cause production of a high molecular weight polyethylene byproduct being a solid phase at room temperature.

In addition, a condition of highly producing the polyethylene product, that is, regions of very low temperature and very high concentration of ethylene may be partially present in the reactor. In the region of very low temperature, the ethylene concentration is locally increased and thus, the production rate of polyethylene polymer is high. When the production amount of the high molecular weight polyethylene being in a solid state at room temperature is increased, the activated catalyst landed on the surface of solid polyethylene is also increased, and the landed catalyst on the surface is likely to cause a abnormally transformed ethylene polymerization reaction by changed electronic and geometric environment around the catalytic center. In addition, when the solid polyethylene polymer on which this catalyst is landed is in an ethylene region of very high concentration at very low temperature, the polymerization rate is drastically accelerated, the molecular weight of the produced polyethylene polymer is very high. These are not present as a suspension but agglomerated together, and as a result, are very likely to cause reactor plugging without being released out of the reactor. Consequently, the root cause of worsening the plugging of the reaction process is a region of very low temperature and a region of very high concentration of ethylene being partially present in the reaction process. Thus, it is important to design the process so that the reaction heat produced in the reaction is removed and the temperature of the reactor is controlled in the reaction process.

Therefore, the problem of the present invention is to minimize the region of very low temperature and the region of very high concentration of ethylene being present partially, and therefrom, to substantially prevent fouling and plugging by the polyethylene polymer which is a byproduct in the reactor and substantially complete a commercialized process.

Therefore, in order to remove reaction heat produced in the reaction and efficiently control the reactor temperature in the selective oligomerization reaction process of ethylene, an object of the present invention is to provide a method of controlling reactor temperature, in a manner of cooling the reaction mixture to be circulated to the reactor and placing an apparatus for separating unreacted ethylene included in the circulation flow so that the concentration of ethylene becomes very low when the reaction mixture is passed through the cooling apparatus, thereby minimizing the production of polyethylene polymer which is a byproduct in the cooling circulation flow, as a method of minimizing a region of very low temperature and a region of very high concentration of ethylene being partially present in the reaction process.

Technical Solution

In one general aspect, a method of preparing an oligomer from ethylene includes: a) oligomerizing ethylene in a reaction solvent in the presence of a catalyst in an ethylene oligomerization reactor; b) separating a first liquid mixture layer including an ethylene oligomer product in the oligomerization reactor of step a) into a first gaseous mixture, and a second liquid mixture layer in a gas-liquid separator; c) cooling the second liquid mixture layer separated from the gas-liquid separator to a lower temperature than an oligomerization reaction temperature of step a) to remove reaction heat produced in step a) and be circulated to the oligomerization reactor; and d) cooling the first gaseous mixture of step b) to be circulated to the oligomerization reactor, as a method of removing reaction heat produced in the oligomerization reaction and controlling temperature of the reactor, in a selective oligomerization reaction process of ethylene.

In the present invention, the ethylene oligomer product may be an ethylene trimer or an ethylene tetramer.

In the present invention, the first gaseous mixture may include unreacted ethylene, a small amount of the ethylene oligomer product, a small amount of the reaction solvent, and a small amount of oligomer byproduct, and the second liquid mixture layer may include a reaction solvent, an ethylene oligomer product, oligomer byproduct, a catalyst, polyethylene byproduct, and a small amount of the unseparated unreacted ethylene.

In the present invention, the oligomerization reactor may have a temperature of 30 to 170° C. and a pressure of 1 to 100 bar, and the gas-liquid separator may have a temperature of 0 to 150° C. and a pressure of 0.1 to 50 bar.

In the present invention, the cooling in steps c) and d) may be carried out at a temperature of −70 to 40° C.

In the present invention, the first liquid mixture layer may be transferred to the gas-liquid separator by pressure difference between the oligomerization reactor and the gas-liquid separator or a flow rate control transfer apparatus.

In the present invention, the above step c) may include separating and removing the polyethylene byproduct from the second liquid mixture layer, and cooling the remaining liquid mixture to be circulated to the oligomerization reactor.

In the present invention, the above step d) may further include separating the first gaseous mixture into a second gaseous mixture including unreacted ethylene, a small amount of the ethylene oligomer product, a small amount of the oligomer byproduct and a small amount of the reaction solvent; and a third liquid mixture layer including a small amount of the unreacted ethylene, the ethylene oligomer product, the oligomer byproduct and the reaction solvent, in a first fractionation column, before cooling.

The method of preparing an oligomer from ethylene of the present invention may further include e) cooling the gaseous layer in the oligomerization reactor of step a) and then transferring it to a second fractionation column to be separated into a third gaseous mixture including the unreacted ethylene and the reaction solvent; and a fourth liquid mixture layer including the ethylene oligomer product, a small amount of the reaction solvent and the oligomer byproduct; and f) cooling the third gaseous mixture of step e) to be circulated to the oligomerization reactor, and transferring the fourth liquid mixture layer to a rear end separation process.

In the present invention, the cooling in steps e) and f) may be carried out at a temperature of −70 to 40° C.

In the present invention, the catalyst of step a) may be a chromium-based organo metalic compound catalyst system produced by a reaction of (1) a chromium compound; (2) a ligand including a pyrrole-based compound or one or more compounds selected from the group consisting of backbone structures of $R_1$—P—C—C—$PR_2$ and $R_3$P—N—$PR_4$; and (3) a cocatalyst, wherein $R_1$ to $R_4$ are independently of one another substituted or unsubstituted hydrocarbyl or heterohydrocarbyl.

Advantageous Effects

The oligomerization reaction process of ethylene according to the present invention may effectively remove reaction heat and control temperature of a reactor, and minimize production of a high molecular weight ethylene polymer byproduct, thereby allowing commercialization of a preparation process of an ethylene trimer and an ethylene tetramer in a high yield.

DETAILED DESCRIPTION OF MAIN ELEMENTS

Figure 1:
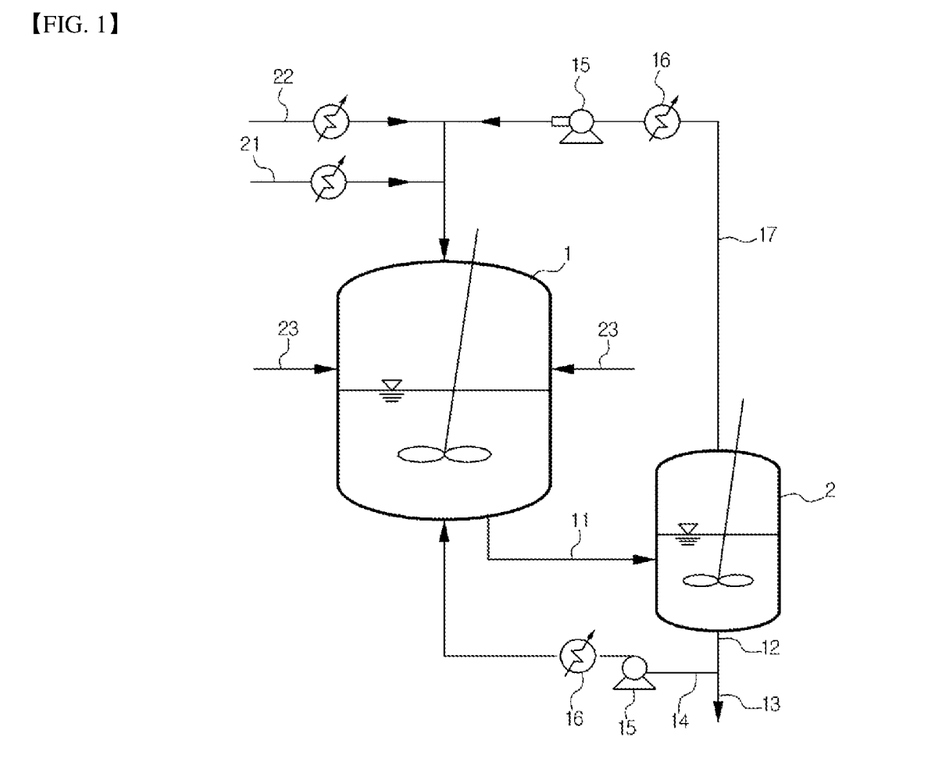
FIG. 1 is a schematic illustration of a process according to a method of preparing an oligomer from ethylene of the present invention.
Figure 2:
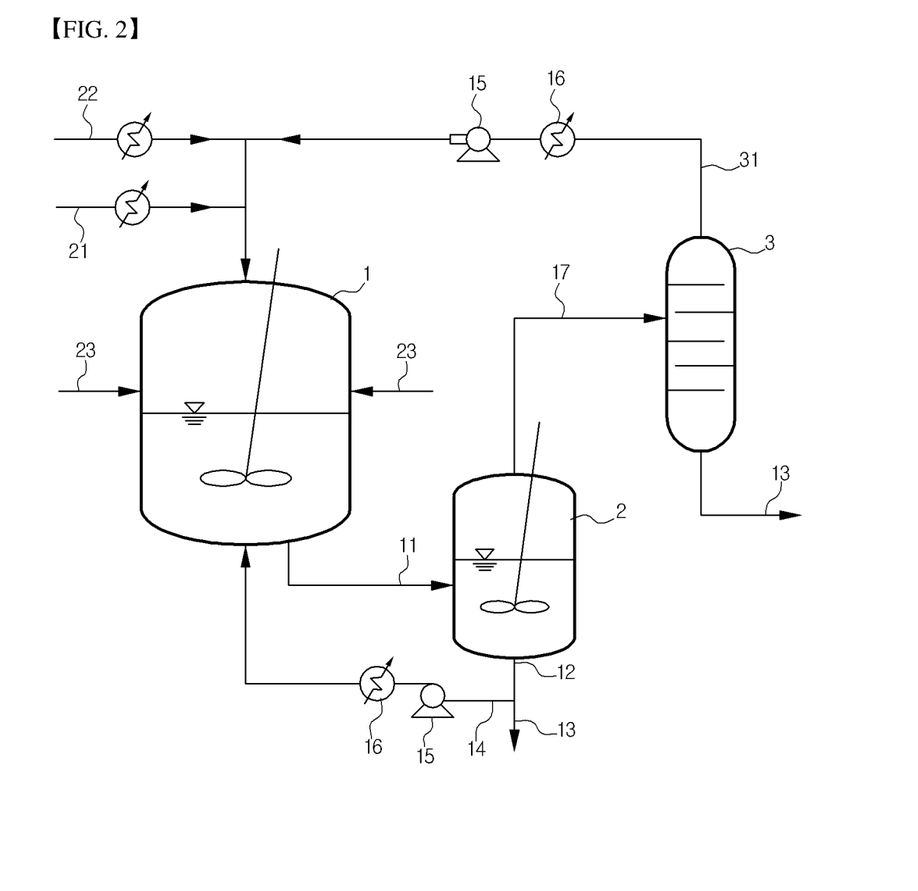
FIG. 2 is a schematic illustration of a process according to a method of preparing an oligomer from ethylene of the present invention.
Figure 3:
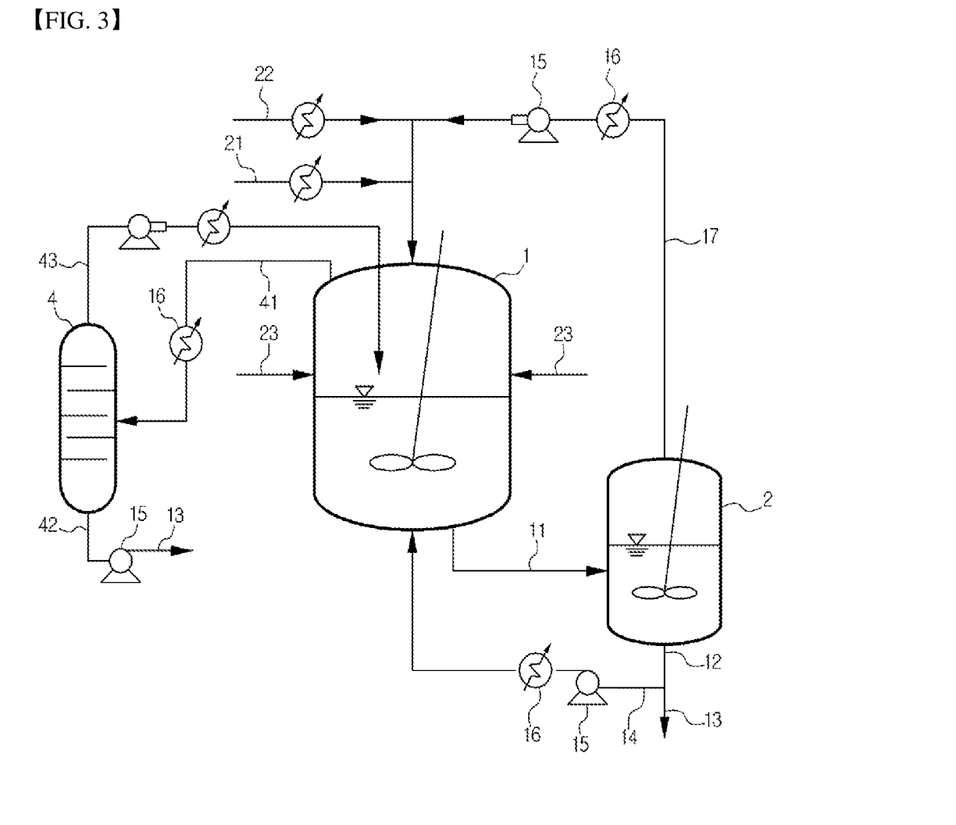
FIG. 3 is a schematic illustration of a process according to a method of preparing an oligomer from ethylene of the present invention.
Figure 4:
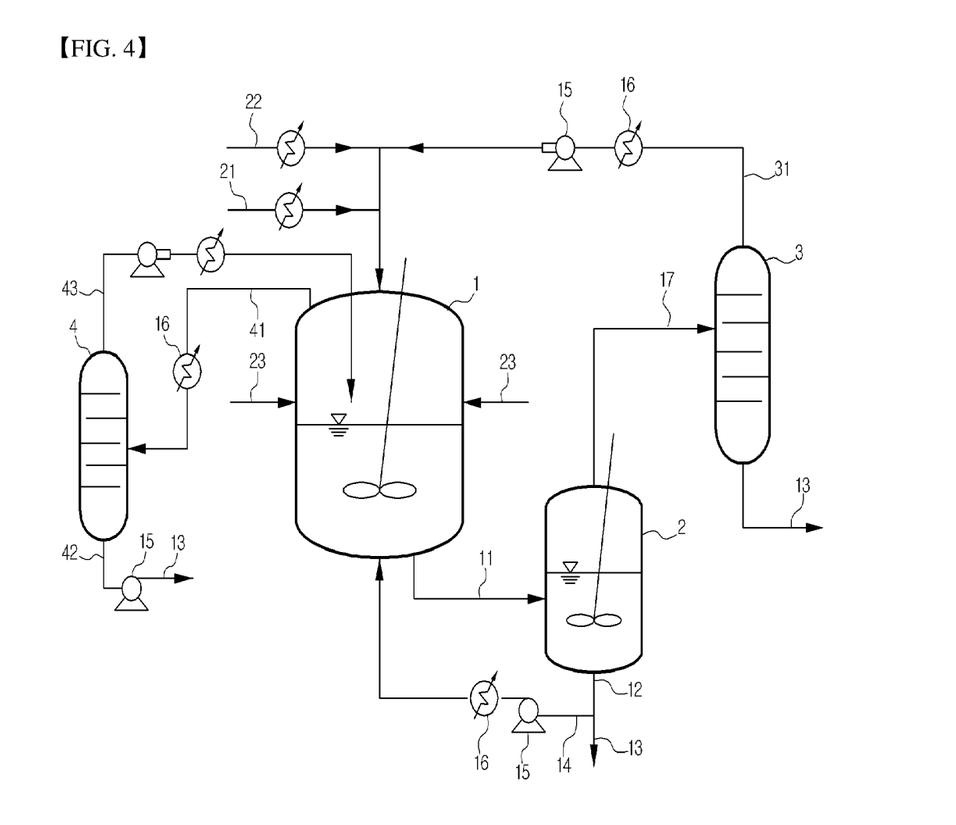
FIG. 4 is a schematic illustration of a process according to a method of preparing an oligomer from ethylene of the present invention.

1: reactor
2: gas-liquid separator
3: first fractionation column
4: second fractionation column
11: first liquid mixture layer transfer flow
12: second liquid mixture layer transfer flow
13: discharge flow
14: second liquid mixture layer circulation flow
15: circulation pump
16: cooler
17: first gaseous mixture transfer flow
21: reaction solvent inlet flow
22: ethylene inlet flow
23: catalyst inlet flow
31: second gaseous mixture circulation flow
41: gaseous layer transfer flow
42: fourth liquid mixture layer transfer flow
43: third gaseous mixture circulation flow

BEST MODE

Hereinafter, the method of preparing an oligomer from ethylene according to the present invention will be described in detail with reference to accompanying drawings. The exemplary embodiments and drawings to be provided below are provided by way of example so that the idea of the present invention may be sufficiently transferred to a person skilled in the art to which the present invention pertains. In addition, technical terms and scientific terms used in the present specification have the general meaning understood by a person skilled in the art unless otherwise defined, and a description for the known function and configuration obscuring the present invention will be omitted in the following description.

Throughout this disclosure, the term "polyethylene byproduct" refers to 'a high molecular weight polyethylene polymer byproduct present in a solid state at a room temperature of 20 to 30° C.' among the products produced from the present invention, and the term "oligomer byproduct" refers to 'an ethylene oligomer byproduct being a liquid phase at room temperature', except for the ethylene trimer and the ethylene tetramer produced from the present invention.

In addition, throughout this disclosure, "substituted" refers to 'in a compound or a structure forming a compound, a hydrogen atom bonded to a carbon atom being substituted with one or more substituents selected from the group consisting of a halogen atom, a nitro group, a hydroxyl group, C1-C7 alkyl, C1-C7 alkoxy, C1-C7 alkylcarbonyl, C1-C7 alkoxycarbonyl, a formyl group (—CHO) and the like'.

The present invention relates to a method of removing reaction heat produced in the oligomerization reaction and controlling temperature of the reactor, in a selective oligomerization reaction process of ethylene, and specifically, a method of preparing an oligomer from ethylene includes: a) oligomerizing ethylene in a reaction solvent in the presence of a catalyst in an ethylene oligomerization reactor; b) separating a first liquid mixture layer including an ethylene oligomer product in the oligomerization reactor of step a) into a first gaseous mixture, and a second liquid mixture layer in a gas-liquid separator; c) cooling the second liquid mixture layer separated from the gas-liquid separator to a lower temperature than an oligomerization reaction temperature of step a) to remove reaction heat produced in step a) and be circulated to the oligomerization reactor; and d) cooling the first gaseous mixture of step b) to be circulated to the oligomerization reactor.

The ethylene oligomer product which is the material to be prepared by the preparation method may be an ethylene trimer and an ethylene tetramer, and more preferably 1-hexene and 1-octene which are commercially useful, but not limited thereto.

The method of preparing an oligomer from ethylene of the present invention may be carried out in a continuous stirred tank reactor (CSTR) or a semi-batch reactor (SBR), but not limited thereto.

In the present invention, the oligomerization reactor in which oligomerization proceeds in step a) may have a temperature of 30 to 170° C., preferably 50 to 120° C., more preferably 60 to 90° C., and a pressure of 1 to 100 bar, preferably 15 to 80 bar, more preferably 30 to 60 bar. The temperature condition of the oligomerization reactor is not particularly limited thereto, but it is preferred to satisfy the range, since the amount of unnecessary polyethylene byproduct produced from the present invention may be minimized, thereby minimizing the possibility of fouling in the reactor and plugging of the reactor outlet and the transfer tube which are process defects being the cause of the polyethylene byproduct. In addition, the pressure condition of the oligomerization reactor is also not particularly limited, but it is preferred to satisfy the range, since an appropriate level of ethylene may be dissolved in a liquid form in a reaction solvent present in the oligomerization reactor, and the oligomerization reaction of ethylene may proceed at a rapid rate.

In the present invention, a liquid layer including an ethylene oligomer product composed of an ethylene trimer and an ethylene tetramer (hereinafter, referred to as a first liquid mixture layer) in the oligomerization reactor may be produced by step a), and the first liquid mixture layer may be separated into a first gaseous mixture and a second liquid mixture layer in a gas-liquid separator in step b), wherein the separated first gaseous mixture may include unreacted ethylene, a small amount of the ethylene oligomer product, a small amount of the reaction solvent and a small amount of the oligomer byproduct, and the second liquid mixture layer may include the reaction solvent, the ethylene oligomer product, 1-hexene and 1-oxtene, the oligomer byproduct, the catalyst, the polyethylene byproduct and a small amount of the unseparated unreacted ethylene.

In the present invention, when the first liquid mixture layer is transferred from the oligomerization reactor to the gas-liquid separator, it may be transferred by pressure difference between the oligomerization reactor and the gas-liquid separator, or by a flow rate control transfer apparatus being present between the oligomerization reactor and the gas-liquid separator, but not particularly limited thereto.

In the present invention, the gas-liquid separator carrying out the separation of the first liquid mixture layer in step b) may use any one separating apparatus selected from the group consisting of a tank type, a column type having a separating end, and a flash drum type, and the gas-liquid separator may include a stirrer for stirring the first liquid mixture layer to be introduced.

The temperature and the pressure of the gas-liquid separator used in the present invention may be in a range lower than the temperature and pressure conditions of the oligomerization reactor, specifically the gas-liquid separator may have a temperature of 0 to 150° C., preferably 15 to 100° C., more preferably 25 to 70° C., and a pressure of 0.1 to 50 bar, preferably 0.5 to 45 bar, more preferably 1 to 30 bar. The temperature and pressure conditions of the gas-liquid separator are not particularly limited, but it is preferred to satisfy the range, since the evaporation reaction of the unreacted ethylene present in the first liquid mixture layer is activated, so that the separation reaction of the first gaseous mixture and the second liquid mixture layer may be effectively carried out. The first gaseous mixture produced from the separation of the first liquid mixture layer may be eluted through an outlet present in an upper portion of the gas-liquid separator, and the second liquid mixture layer may be eluted through an outlet present in a lower portion of the gas-liquid separator.

The second liquid mixture layer separated in step b) of the present invention may be eluted from the gas-liquid separator to be recirculated to the oligomerization reactor in step c). Here, the above step c) of the present invention may include separating polyethylene byproduct from the second liquid mixture layer and cooling the remaining liquid mixture to be circulated to the oligomerization reactor, and the separation step may be carried out by a filter or a centrifuge, however, the present invention is not particularly limited thereto. By removing the solid polyethylene byproduct from the oligomerization reaction circulation flow in the above separation step, the possibility of occurrence of fouling in the reactor and plugging of the reactor outlet and the transfer tube, caused by the polyethylene byproduct reintroduced to the oligomerization reactor may be minimized. In addition, the liquid mixture from which the polyethylene byproduct is separated by the separation step may be cooled to a lower temperature than the temperature of the oligomerization reactor of the present invention by the cooling apparatus to be circulated to the oligomerization reactor.

In the present invention, the cooling in step c) may be carried out at a temperature of −70 to 40° C., preferably of −40 to 30° C. The cooling temperature condition of the separated liquid mixture is not particularly limited, but it is most preferred to satisfy the above range, since the reaction heat in the oligomerization reactor may be effectively removed by introducing the cooled liquid mixture to the oligomerization reactor, which allows the temperature control of the oligomerization reactor, thereby minimizing the production possibility of the polyethylene byproduct in a solid state caused by abrupt temperature change of the reactor.

In addition, in the present invention, the above step d) may further include a separation step of eluting and transferring the first gaseous mixture from the gas-liquid separator to be separated into a second gaseous mixture including unreacted ethylene, a small amount of the ethylene oligomer product, a small amount of the oligomer byproduct and a small amount of the reaction solvent; and a third liquid mixture layer including a small amount of the unreacted ethylene, the ethylene oligomer product, the oligomer byproduct and the reaction solvent, in a first fractionation column, before cooling (hereinafter, referred to as the separation step in step d)). The first fractionation column may have a temperature of 5 to 50° C., preferably of 10 to 25° C., and a pressure of 0 to 10 bar. The temperature and pressure conditions of the first fractionation column are not particularly limited, but it is preferred to satisfy the range, since the separation reaction of the second gaseous mixture and the third liquid mixture layer from the first gaseous mixture may be effectively carried out. The second gaseous mixture produced from the separation of the first gaseous mixture may be eluted through an outlet present in an upper portion of the first fractionation column, and the third liquid mixture layer may be eluted through an outlet present in a lower portion of the first fractionation column. By the elution, the third liquid mixture layer may be transferred to a rear end separation process, and by the rear end separation process, the ethylene trimer and the ethylene tetramer which are the ethylene oligomer product of the present invention may be obtained in a separate form. The rear end separation process of the present invention may be any process as long as it is used for separating the components of a liquid mixture, and preferably may include distillation by a distillation apparatus, but not particularly limited thereto.

In the present invention, the first gaseous mixture of step d), or the second gaseous mixture including unreacted ethylene, a small amount of the ethylene oligomer product, a small amount of the oligomer byproduct and a small amount of the reaction solvent in a gaseous state, produced from the separation step in step d) may be cooled to a lower temperature than the temperature of the oligomerization reactor of the present invention by the cooling apparatus through cooling of step d) of the present invention to be circulated to the oligomerization reactor.

In the present invention, the cooling in step d) may be carried out at a temperature of −70 to 40° C., preferably of −40 to 10° C. The cooling temperature condition of step d) is not particularly limited, but it is preferred to cool the first gaseous mixture or the second gaseous mixture to the above temperature range, since the operation energy cost of the gaseous mixture is low, and thus, economical, and the process may be simplified. The first gaseous mixture or the second gaseous mixture cooled in step d) of the present invention may be circulated into the reactor by a pressure apparatus, but not particularly limited thereto.

In addition, the method of preparing an oligomer from ethylene of the present invention may further include e) cooling the gaseous layer in the oligomerization reactor of step a) and then transferring it to a second fractionation column to separate the gaseous layer into a third gaseous mixture including the unreacted ethylene and the reaction solvent in a gaseous state; and a fourth liquid mixture layer including the ethylene oligomer product, a small amount of the reaction solvent and the oligomer byproduct; and f) cooling the third gaseous mixture of step e) to be circulated to the oligomerization reactor, and transferring the fourth liquid mixture layer to a rear end separation process.

The above steps e) and f) of the present invention may be carried out simultaneously with step b) of the present invention after step a), or after step d) of the present invention, but it not particularly limited thereto.

In the present invention, the first liquid mixture layer including the ethylene oligomer product in the oligomerization reactor, and also the gaseous layer including a small amount of the ethylene oligomer product and the oligomer byproduct, the unreacted ethylene and the reaction solvent in a gaseous state may be produced by the ethylene oligomerization reaction of step a), and the gaseous layer may be eluted into the outlet present in the upper portion of the oligomerization reactor. The eluted gaseous layer may be cooled through step e), and then transferred to the second fractionation column to be separated into the third gaseous mixture and the fourth liquid mixture layer. In step e) of the present invention, the gaseous layer may be cooled to a temperature of −70 to 40° C., preferably −40 to 20° C., but not particularly limited thereto.

In addition, the second fractionation column used in step e) of the present invention may have a temperature of 5 to 50° C., preferably of 10 to 25° C., and a pressure of 0 to 10 bar. The temperature and pressure conditions of the second fractionation column are not particularly limited, but it is preferred to satisfy the range, since the separation reaction of the third gaseous mixture and the fourth liquid mixture layer from the gaseous layer may be effectively carried out.

The third gaseous mixture produced from the separation of the gaseous layer may be eluted through an outlet present in an upper portion of the second fractionation column, and the fourth liquid mixture layer may be eluted through an outlet present in a lower portion of the second fractionation column. By the elution, the fourth liquid mixture layer may be transferred to the rear end separation process of the present invention, and the ethylene trimer and the ethylene tetramer which are the ethylene oligomer product in the reaction circulation flow of the present invention may be obtained in a separate form thereby.

In addition, the third gaseous mixture including unreacted ethylene and the reaction solvent in a gaseous state, produced from the separation step in step e) of the present invention may be cooled to a lower temperature than the temperature of the oligomerization reactor of the present invention by the cooling apparatus through step f) of the present invention to be circulated to the oligomerization reactor.

In the present invention, the cooling in step f) may be carried out at a temperature of −70 to 40° C., preferably of −40 to 10° C. The cooling temperature condition of the separated third gaseous mixture is not particularly limited, but it is preferred to cool the third gaseous mixture to the above temperature range, since the operation energy cost of the third gaseous mixture is low, and thus, economical, and the process may be simplified. The third gaseous mixture cooled in step f) of the present invention may be circulated into the reactor by a pressure apparatus, but not particularly limited thereto.

The catalyst of step a) which may be used in the method of preparing an oligomer from ethylene of the present invention may be an organo metalic compound catalyst system produced by a reaction of (1) a chromium compound; (2) ligand including a pyrrole-based compound or one or more compounds selected from the group consisting of backbone structures of $R_1P$—C—C—$PR_2$ (hereinafter, referred to as P—C—C—P) and $R_3P$—N—$PR_4$; and (3) a cocatalyst. Here, $R_1$ to $R_4$ may be independently of one another substituted or unsubstituted hydrocarbyl or substituted or unsubstituted heterohydrocarbyl, preferably independently of one another any one selected from the group consisting of phenyl, benzyl, naphthyl, anthracenyl, mesityl, xylyl, methyl, ethyl, ethylenyl, propyl, propenyl, propynyl, butyl, cyclohexyl, 4-methylcyclohexyl, 4-ethylcyclohexyl, 4-isopropylcyclohexyl, tolyl, xylyl, 4-methylphenyl, 4-ethylphenyl, 4-isopropylphenyl, 4-t-butylphenyl, 4-methoxyphenyl, 4-isopropoxyphenyl, cumyl, methoxy, ethoxy, phenoxy, tolyloxy, dimethylamino, thiomethyl, trimethylsylyl, dimetylhydrizyl, 2-methylcyclohexyl, 2-ethylcyclohexyl, 2-isopropylcyclohexyl, o-methylphenyl, o-ethylphenyl, o-isopropylphenyl, o-t-butylphenyl, o-methoxyphenyl, o-isopropoxyphenyl, biphenyl, naphthyl, anthracenyl and the like, but not limited thereto.

In the present invention, the chromium-based organo metalic compound used as the catalyst may be a chromium-based organo metalic complex having chromium as a center metal, and coordinated with ligand compounds including one or more of nitrogen, oxygen, sulfur or phosphorus atoms having unshared electron pairs, and the compound may be produced by a combination of a cocatalyst activating the chromium complex in addition to the chromium complex. The chromium compound and the ligand which are the precursors of the complex may be used, respectively, in the reaction in place of the chromium organo metalic complex. The chromium compound used for producing the catalyst of the present invention may be one or more selected from the group consisting of chromium(III) (acetylacetonate)$_3$, chromium trichloride tristetrahydrofuran, chromium(III)2-ethylhexanoate and the like. In addition, the ligand used in the catalyst of the present invention may be preferably one or more selected from the group consisting of pyrrole, dialkylpyrrole, (phenyl)$_2$-P—N(isopropyl)-P(phenyl)$_2$, (phenyl)$_2$-P—CH(methyl)CH(methyl)-P(phenyl)$_2$, (o-methoxyphenyl)$_2$-P—CH(methyl)CH(methyl)-P(o-methoxyphenyl)$_2$ and (p-methoxyphenyl)$_2$-P—CH(methyl)CH(methyl)-P(p-methoxyphenyl)$_2$ and the like, but not limited thereto. The chromium-based organo metalic complex used in the present invention may be a compound synthesized by a reaction of the chromium compound and the ligand under an organic solvent, and most preferably chromium trichloride tristetrahydrofuran as the chromium compound, and bis-[(phenyl)$_2$-P—CH(methyl)CH(methyl)-P(phenyl)$_2$chromium dichloride(μ-chloride)] synthesized by a reaction of (phenyl)$_2$-P—CH(methyl)CH(methyl)-P(phenyl)$_2$ as the ligand, but not particularly limited thereto. The cocatalyst used in the catalyst of the present invention may be alkylaluminum or partially oxidized aluminoxane of alkylaluminum, and used differently depending on the kind of ligand. More specifically, in the case that the ligand used in the present invention is the pyrrole-based compound, alkylhalide-added alkylaluminum may be used as the cocatalyst, and in the case that the used ligand is one or more compounds selected from the group consisting of the backbone structures of $R_1P$—C—C—$PR_2$ (hereinafter, referred to as P—C—C—P) and $R_3P$—N—$PR_4$, aluminoxane may be used as the cocatalyst. Here, the aluminoxane may be preferably partially oxidized methylaluminoxane (MAO) of trimethylaluminum (AlMe$_3$, TMA), or modified methylaluminoxane (MMAO) by partially oxidized triisobutylaluminum (Al(i-Bu)$_3$, TIBA) and TMA, but not limited thereto.

The invention claimed is:

1. A method of preparing an ethylene oligomer product comprising:
   a) oligomerizing ethylene in a reaction solvent in the presence of a catalyst in an ethylene oligomerization reactor to produce a first liquid effluent comprising the ethylene oligomer product;
   b) passing the first liquid effluent into a gas-liquid separator to obtain a first gaseous mixture comprising unreacted ethylene and a second liquid mixture comprising the reaction solvent, the ethylene oligomer product, an oligomer byproduct, the catalyst, and a polyethylene byproduct;
   c) cooling the second liquid mixture in a first cooler to a lower temperature than the ethylene oligomerization reaction temperature, and recycling the cooled second liquid mixture into a first inlet of the oligomerization reactor; and
   d) cooling the first gaseous mixture in a second cooler and recycling the cooled first gaseous mixture into a second inlet of the oligomerization reactor;
   wherein the oligomer byproduct is an ethylene oligomer byproduct being a liquid phase at room temperature, and
   wherein the polyethylene byproduct is present in a solid state at room temperature.

2. The method of claim 1, wherein the ethylene oligomer product is an ethylene trimer and an ethylene tetramer.

3. The method of claim 1, wherein the oligomerization reactor has a temperature of 30 to 170° C. and a pressure of 1 to 100 bar, and the gas-liquid separator has a temperature of 0 to 150° C. and a pressure of 0.1 to 50 bar.

4. The method of claim 1, wherein the cooling in c) and d) is carried out at a temperature of −70 to 40° C.

5. The method of claim 1, wherein the first liquid effluent is transferred to the gas-liquid separator by pressure difference between the oligomerization reactor and the gas-liquid separator or a flow rate control transfer apparatus.

6. The method of claim 1, wherein c) includes separating and removing polyethylene byproduct from the second liquid mixture layer, and cooling a remaining liquid mixture to be circulated to the oligomerization reactor.

7. The method of claim 1, further comprising:
   separating from the first gaseous mixture in a first fractionation column a third liquid mixture comprising ethylene oligomer product, oligomer byproduct and reaction solvent.

8. The method of claim 1, further comprising:
   e) cooling a gaseous effluent from the oligomerization reactor and transferring the cooled gaseous effluent to a second fractionation column to separate a third gaseous mixture comprising unreacted ethylene and reaction solvent and a fourth liquid mixture comprising ethylene oligomer product and oligomer byproduct; and
   f) cooling the third gaseous mixture and recycling the cooled third gaseous mixture to the oligomerization reactor, and transferring the fourth liquid mixture layer to a rear end separation process.

9. The method of claim 8, wherein the cooling in e) and f) is carried out at a temperature of −70 to 40° C.

10. The method of claim 1, wherein the catalyst of a) is a chromium-based organo metalic compound catalyst system produced by a reaction of (1) a chromium compound; (2) a ligand including a pyrrole-based compound or one or more compounds selected from the group consisting of backbone structures of $R_1P$—C—C—$PR_2$ and $R_3P$—N—$PR_4$; and (3) a cocatalyst (wherein $R_1$ to $R_4$ are independently of one another substituted or unsubstituted hydrocarbyl, or substituted or unsubstituted heterohydrocarbyl).

* * * * *